United States Patent [19]

Yanagawa

[11] Patent Number: 5,603,943
[45] Date of Patent: Feb. 18, 1997

[54] NASALLY ADMINISTRABLE COMPOSITIONS

[75] Inventor: Akira Yanagawa, Yokohama, Japan

[73] Assignee: Dott Research Laboratory, Yokohama, Japan

[21] Appl. No.: 429,501

[22] Filed: Apr. 26, 1995

[30] Foreign Application Priority Data

May 11, 1994 [JP] Japan ............................. 6-120778
Mar. 2, 1995 [JP] Japan ............................. 7-066640

[51] Int. Cl.⁶ ........................... A61K 9/14; A61K 9/50
[52] U.S. Cl. ..................... 424/434; 424/489; 424/501; 514/785
[58] Field of Search ........................ 424/434, 484, 424/501; 514/785

[56] References Cited

U.S. PATENT DOCUMENTS 4,659,696  4/1987  Hirai et al. ........................... 514/15

FOREIGN PATENT DOCUMENTS 0-588-255  3/1994  European Pat. Off. .
0-648-498  4/1995  European Pat. Off. .
206922     7/1993  Japan .
5-255095   10/1993 Japan .

*Primary Examiner*—Carlos Azpuru
*Attorney, Agent, or Firm*—Foley & Lardner

[57] ABSTRACT

A nasally administrable composition having a physiologically active substance dispersed homogeneously in and adsorbed homogeneously onto a unique carrier. The nasally administrable composition contains a physiologically effective amount of the physiologically active substance having a molecular weight of not more than 40,000, dispersed homogeneously in and adsorbed homogeneously onto physiologically acceptable powdery or crystalline polyvalence metal compound carrier.

The metal compound carrier is selected from aluminum compound, calcium compound, magnesium compound, silicon compound, iron compound and zinc compound.

The composition is nasally administrable in powdery form.

26 Claims, No Drawings

NASALLY ADMINISTRABLE COMPOSITIONS

BACKGROUND OF THE INVENTION

1. Field of the Invention

The present invention relates to a nasally administrable composition containing a physiologically active substance, which attains high stability in the form of a preparation and improved absorbability of said physiologically active substance into the body, when administered nasally.

2. Description of the Prior Art

Physiologically active peptides such as calcitonin and insulin are polymers which are extensively employed for medical usage in clinical practice, due to their specific physiological activity.

These physiologically active peptides, however, can little be absorbed intact from the mucous membrane of the intestine because they are likely to be decomposed with proteases existing in the digestive system or are high in molecular weight and polarity. Hence, they cannot be administered orally and they can be administered only through injection. The injectable administration cannot be said to be preferable because the injection causes pain at the site of injection to patients. In addition, particularly, when the injection should be repeated at constant intervals, such pain is repeated whenever they are injected and it may often become too severe for patients to endure. Therefore, strong demand has been made to develop a method for administering the physiologically active peptide via a non-injection route and, more preferably, a method which enable patients to administer it by themselves, which further should be safe, simple in administration and administrable with less frequency.

As one of such methods for administering the physiologically active peptides, an aerosol in the form of a suspension, which uses a fluorinated hydrocarbon as a spouting agent, has been developed for nasally administering, for example, calcitonin. As another means for nasal administration, a spraying agent has been proposed as a nasally administrable liquid preparation, which is a preparation in which calcitonin is formulated with a surface-active agent as an absorption promoter. Furthermore, recently, there have been proposed some nasally administrable powdery preparations having improved absorbability, which are prepared by adsorbing calcitonin onto a polysaccharide such as cellulose.

On the other hand, up to now, there have been developed a great many synthetic medicaments for various therapeutical purposes; however, there have not been developed into datails for nasally administrable preparations containing said medicaments.

The various techniques for nasal administration, which have most recently been actively developed, are said to be in principle superior as methods for administering such physiologically active peptides as unlikely to be administered orally or as well as for administering such synthetic medicaments. Since the plexus venosus develops at the nasal lamina propria mucosae of the nasal cavity, the physiologically active peptide or the synthetic medicament, when administered nasally, is absorbed through the mucous membrane of the nasal cavity into the circulatory system of the body; however, nasally administrable preparations so far proposed are not satisfactory because of poor absorbability of the active ingredient or local irritation so that they are not commercially available yet.

SUMMARY OF THE INVENTION

The present invention has the primary object to provide a nasally administrable composition to nasally administer such a physiologically active peptide or other physiologically active substances as unlikely to be administered orally, with higher bioavailability and less irritation than those of other nasally administrable preparations so far proposed.

As a result of extensive studies and researches on such nasally administrable preparations to achieve the object of the present invention, the present inventor has found that a composition, which is prepared by homogeneously dispersing the physiologically active peptide, such as calcitonin or insulin, in unique carrier, i.e. a physiologocally acceptable polyvalence metal carrier having a mean particle size of not more than 250 µm, which has not yet been studied as a carrier for use with a nasally administrable preparation, and by homogeneously adsorbing it onto the carrier, is administrable via a nasal route—in other words, that the composition can be applied to the mucous membrane of the nasal cavity—to thereby allow a clinically effective treatment.

Furthermore, the present inventor has found that a nasally administrable composition of other synthetic medicaments, which is prepared by homogeneously dispersing the active substance in the same polyvalence metal carrier can also attain equal or higher clinincal effectiveness compared with those administered orally.

In other words, it has been found by the present inventor that the technique of homogeneously dispersing a physiologically active peptide such as calcitonin and insulin, or other physiologically active substance in a unique carrier and adsorbing said peptide or substance onto the carrier provides an equal or higher bioavailability compared with that obtained by injection or oral adminstration.

The present invention has been completed on the basis of these findings.

As described hereinabove, the primary object of the present invention is to provide a nasally administrable composition comprising a physiologically active substance having a molecular weight of not more than 40,000 and a physiologically acceptable powdery or crystalline polyvalence metal carrier, wherein a physiologically effective amount of said physiologically active substance is dispersed homogeneously in and adsorbed homogenously onto said polyvalence metal carrier, and a mean particle size of said polyvalence metal carrier is not more than 250 µm.

Other objects, features and advantages of the present invention will become apparent in the course of the description of preferred embodiments.

DETAILED DESCRIPTION OF THE INVENTION

Active substance to be contained in the composition may be any phsiologically active substance which has a molecular weight of not more than 40,000 and is nasally administrable.

The physiologically active substance to be used in the present invention may be any one of those employed as ordinary pharmaceuticals, of which examples will be mentioned later.

The physiologically acceptable polyvalence metal carrier used as the carrier of the present invention may be metal compound having more than 2 valency, and may include, for example, aluminum compound, calcium compound, magnesium compound, silicon compound, iron compound and zinc compound. These metal compounds are commonly used as an excipient, stabilizer, filling agent, distingrator, lubricant, adsorbent and coating agent for a medical perparation, but nothing has been so far reviewed about the applicability to a carrier for a nasally administrable preparation.

The aluminum compound to be used as a carrier of the present invention may include, for example, dry aluminum hydroxy gel, aluminum hydroxychloride, synthetic aluminum silicate, light aluminum oxide, colloidal aluminum silicate hydrate, aluminum magnesium hydroxide, aluminum hydroxide, aluminum hydroxide gel, aluminum sulfate, dihydroxyaluminum aminoacetate, aluminum stearate, natural aluminum silicate, aluminum monostearate and potassium aluminum sulfate.

The calcium compound may include, for example, apatite, hydroxyapatite, calcium carbonate, calcium disodium EDTA, calcium chloride, calcium citrate, calcium glycerophosphate, calcium gluconate, calcium silicate, calcium oxide, calcium hydroxide, calcium stearate, calcium phosphate tribasic, calcium lactate, calcium pantothenate, calcium oleate, calcium palmirate, calcium D-pantothenate, calcium alginate, calcium phosphate anhydride, calcium hydrogenphosphate, calcium primary phosphate, calcium acetate, calcium saccharate, calcium sulfate, calcium secondary phosphate, calcium para-aminosalicylate, and bio calcilutite compounds.

Furthermore, the magnesium compound used in the composition of the present invention includes, for example, magnesium L-aspartate, magnesium chloride, magnesium gluconate, magnesium aluminate silicate, magnesium silicate, magnesium oxide, magnesium hydroxide, magnesium stearate, magnesium carbonate, magnesium aluminate metasilicate, magnesium sulfate, sodium magnesium silicate and synthetic sodium magnesium silicate.

Other divalence metal compounds may be silicon compound such as silicon oxide hydrate, light silicic anhydride, synthetic hydrotalcite, diatomaceous earth and silicon dioxide; iron compound such as ferrous sulfate; and zinc compound such as zinc chloride, zinc stearate, zinc oxide and zinc sulfate.

The above metal carriers may be used alone or in combination of two or more.

The metal compound to be used as the carrier of the present invention may have a mean particle size of not more than 250 μm, preferably not more than 100 μm, and more preferably from 30 μm to 60 μm.

Among them, calcium compounds such as hydroxyapatite, calcium carbonate and calcium lactate; magnesium compounds such as magnesium stearate; and aluminum compounds such as hydroxy aluminum are particularly preferred.

Hydroxyapatite ($Ca_{10}(PO_4)_6(OH)_2$), which is a preferable carrier in the present invention, is a main component of inorganic materials in hard tissues such as bones or tooth roots, and it is used for coating substance of implants for bones, joints and tooth roots so far.

It should be noted herein, however, that nothing has been so far reviewed about the applicability to a carrier for a nasally administrable preparation and the present inventor is the first to have discovered the applicability.

Bio calcilutite compounds such as crystalline calcium pyrophosphate ($Ca_2P_2O_7$ $2H_2O$), calcium secondary phosphate ($CaHPO_4$ $2H_2O$), octacalcium phosphate ($Ca_8H_2(PO_4)$ $5H_2O$), tricalcium phosphate ($Ca_3(PO_4)_2$) and crystalline calcium oxalate ($CaC_2O_4$ $H_2O$) are analogous to hydroxyapatite, and may also be used as the carrier of the present invention.

For nasally administrable preparations, it has been thought so far that a water-soluble carrier would help to attain a good absorption of the active substance into the body. However, the present inventor found that an excellent absorption of active substances is obtainable by homogeneously dispersing the active substance in a water-insoluble carrier, for example, hydroxyapatite, calcium carbonate, calcium lactate, aluminum hydroxide or magnesium stearate, and homogeneously adsorbing said active substance thereonto.

The hydroxyapatite used in the present invention includes synthetic hydroxyapatite and hydroxyapatite obtained from organisms (bio-hydroxyapatite). The bio-hydroxyapatite may be prepared by using bones or teeth of animals from which organic materials are removed.

Calcium carbonate, calcium lactate, aluminum hydroxide or magnesium stearate is usually used as a stabilizer, lubricant, agent to add luster, excipient, dispersing agent or coating agent for a pharmaceutical preparation; however, the present inventor found that these compounds having a mean particle size of not more than 250 μm can be used as the carrier for the composition of the present invention, and offers the effect of promoting the absorption of physiologically active substance into the body by nasal administration.

On the other hand, physiologically active substances having a molecular weight of not more than 40,000 to be contained in the composition of the present invention may be any one of those employed as ordinary pharmaceuticals, for example, physiologically active peptides, hypnotics and sedatives, anti-epileptics, minor tranquilizer, major tranquilizer, antidepressants, muscle relaxants, anti-allergic agents, antirheumatics, cardiotonics, antiarrhythmic agents, antihypertensive diuretics, α-blocking agents, β-adrenergic blocking agents, calcium channel antagonists, angiotensin converting enzyme inhibitors (AEC inhibitors), antihypertensives, coronary vasodilators, cerebral circulation and metabolism ameliorators, anti-arteriosclerotic agents, cardiovascular agents, bronchodilators, anti-ulceratives, antiemetics, antiobesity agents, platelet aggregation inhibitors, antidiabetics/symptomatic antidiabetics, adrenocortical hormones, DNA/RNA compounds and so on.

Therefore, a prefarable mode of the composition according to the present invention is a nasally administrable composition comprising a physiologically active substance and a physiologically acceptable powdery or crystalline polyvalence metal carrier, wherein an effective amount of the physiologically active substance selected from the group consisting of physiologically active peptides, hypnotics and sedatives, anti-epileptics, minor tranquilizer, major tranquilizer, antidepressants, muscle relaxants, anti-allergic agents, antirheumatics, cardiotonics, antiarrhythmic agents, antihypertensive diuretics, α-blocking agents, β-adrenergic blocking agents, calcium channel antagonists, angiotensin converting enzyme inhibitors (AEC inhibitors), antihypertensives, coronary vasodilators, cerebral circulation and metabolism ameliorators, anti-arteriosclerotic agents, cardiovascular agents, bronchodilators, anti-ulceratives, antiemetics, antiobesity agents, platelet aggregation inhibitors, antidiabetics/symptomatic antidiabetics, adrenocortical hormones, and DNA/RNA compounds, is dispersed homogeneously in and adsorbed homogeneously onto the polyvalence metal carrier whose mean particle size is not more than 250 μm, preferably not more than 100 μm and more preferably from 30 μm to 60 μm.

It is to be noted herein that the physiologically active substances to be used for the present invention are not necessarily limited to those on the market, but may be those under clinical development.

The physiologically active substances to be used as an active ingredient of the composition of the present invention may include hypnotics and sedatives such as lormetazepam, quazepam and zolpidem; anti-epileptics such as sadium valproate and vigabatrin; minor tranquilizers such as diazepam, buspirone and suriclone; major traquilizers such as ceruletide diethylamine, emonapride, risperidone and mosapramine; antidepressants such as trazodone, fluvoxamine, zimeldine and rolipram; muscle relaxants such as inaperisone and cimetropium; anti-allergic agents such as pemirolast, tazanolast, traxanox, dolkast, emedastine, loratadine, cetirizine, suplatast, seratrodast, batabulast, doqualast, butenafine, pentigetide, picumast and levocabastine; antirheumatics such as salazosulfapyridine, nuclomedone, platonin and actarit; cardiotonics such as xamoterol, vesnarinone, nitroprusside, amrinone, docarpamine, isosorbide, ibopamine, enoximone, loprinone, fenoldopam, pimobendan and milrinone; antiarrhythmic agents such as flecainide, pilsicainide, cibenzoline, bepridil, amiodaron, pentisomide, pirmenol and moracizine; antihypertensive diuretics such as carperitide and torasemide; α-adrenergic blocking agents such as doxazocine, tamsulosin and bunazosin; β-adrenergic blocking agents such as carvedilol, bisoprolol, tilisolol, xibenolol, celiprolol, metoprolol, cateolol, bopindolol, betaxolol and bevantolol; calcium channel antagonists such as bepridil, nisoldipine, nimodipine, nitrendipine, lomerizine, benidipine, gallopamil, manidipine, palonidipine, barnidipine, fasudil, cilnidipine, semotiadil, amlodipine, efonidipine, diltiazem, clentiazem, lacidipine, felodipine, niludipine, lemakalim, asanidipine, pranidipine, isradipine and dazodipine; angiotensin converting enzyme inhibitors such as moveltripril, cilazapril, ramipril, lisinopril, temocapril, spirapril, imidapril, benazepril, quinapril and fosinopril; antihypertensives such as ketanserin, pinacidil, diazoxide, naftopidil, clonidine, flosequinan and cromakalim; coronary vasodilators such as isosorbide and molsidomine; cerebral circulation and metabolism ameliorators such as ademetionine, dihydroergotoxine, aniracetam, noftidrofuryl, teniloxazine, minaprine, bufromedil, oxiracetam, azetirelin, vinconate, erythritol, fasudil, amiridin, tamolarizine, nebracetam and elziverine; anti-arteriosclerotic agents such as bezafibrate, colestyramine and simvastatin; cardiovascular agents such as levocarnitine and alinidine; bronchodilators such as oxitropium bromide, theophylline, ozagrel, salmeterol and tulobuterol; anti-ulceratives such as proamipide, misoprostol, nizatidine, enprostil, arbaprostil, rotraxate, triimoprostil, omeprazole, beperidium iodide, lansoprazole, nizatidine, rioprostil, polaprezinc, leminoprazole, mezolidone and nocloprost; antiemetics such as granisetron, ondansetron, azasetron, domperidone and cisapride; antiobesity agents such as mazindol; platelet aggregation inhibitors such as dalteparin, argatroban, iloprost, ataprost, beraprost, carbacyclin, isbogrel, sarpogrelate, satigrel and clopidogrel; antidiabetics/symptomatic antidiabetics such as pioglitazone, voglibose, gliclazide, acarbose, ciglitazone, sorbinil, glimepiride, epalrestat, cronassial, midaglizole and ponalrestat; adrenocortical hormone preparations such as hydrocortisone, prednisolone, triamcinolone, dexamethasone, flunisolide, fluorometholone, hydrocortisone fumalate, paramethasone acetate, betamethasone; and DNA/RNA compounds such as DNA vector, RNA vector and antisence DNA in the gene therapy.

In this connection, it should be noted that the above names of medicaments are International Nonproprietary Name (INN) for pharmaceutical substances or Japanese Accepted Names (JAN) for pharmaceuticals.

Among those physiologically active substances as described hereinabove, physiologically active peptides are preferred.

The physiologically active peptides may include peptide hormones, physiologically active proteins and enzymatic proteins.

The peptide hormones may include, for example, parathormone (parathyroid hormone), calcitonin, insulin, angiotensin, glucagon, gastrin, secretin, growth hormone, prolactin (luteotropic hormone), gonadotropin (gonodotropic hormone), thyrotropic hormone, adrenocorticotropic hormone, melanocyte stimulating hormone, vasopressin, oxytocin, protirelin, luteinizing hormone releasing hormone, corticotropin, somatotropin (somatropin), thyrotropin (thyroid stimulating hormone), somatostatin (growth hormone inhibiting factor), G-CSF, erythropoietin, superoxide dismutase (SOD), and so on.

In addition, interferons, interleukins, urokinases, lysozymes, vaccines and so on may also be used as the physiologically active peptide.

It is to be noted herein that the physiologically active peptides to be used for the present invention are not restricted to those described hereinabove and that any nasally administrable physiologically active peptide may be formulated into the composition according to the present invention.

Among those physiologically active peptides as described hereinabove, the peptide hormones are preferred. Further, among the peptide hormones, calcitonin, insulin, somatropin and glucagon are preferred, among which calcitonin and insulin are particularly preferred.

Calcitonins to be preferably employed for the composition according to the present invention may include, for example, salmon calcitonin, human calcitonin, hog calcitonin, chicken calcitonin, cattle calcitonin, eel calcitonin, and so on. These calcitonins are naturally occurring ones that are to be extracted from the origin and that are commercially available. It can be noted herein that eel calcitonin is higher in stability than human calcitonin that in turn is higher than salmon calcitonin; however, even the salmon calcitonin relatively low in stability, being homogeneously dispersed in and adsorbed onto the unique carrier to be used for the present invention, can be a physiologically active peptide composition that is high both in bioavailability and concentration in blood. Therefore, calcitonins are most suitable as the physiologically active peptide for the present invention.

Hence, one preferable mode of the composition according to the the present invention is a physiologically active peptide composition in powdery form, which is formulated into a nasally administrable preparation, in which a physiologically effective amount of physiologically active peptide is homogeneously dispersed in and adsorbed onto a divalence metal carrier selected from aluminum compound, calcium compound, magnesium compound, silicon compound, iron compound and zinc compound, whose mean particle size is not more than 250 μm, preferably not more than 100 μm and more preferably 30 μm to 60 μm.

Another preferable mode of the composition according to the the present invention is a nasally administrable physiologically active peptide composition in powdery form, in which a physiologically effective amount of physiologically active peptide is homogeneously dispersed in and adsorbed onto the carrier selected from hydroxyapatite, calcium carbonate, calcium lactate, magnesium stearate whose mean particle size is not more than 100 µm.

Furthermore, the most preferable mode of the composition according to the present invention is a nasally administrable physiologically active peptide composition in powdery form, in which a physiologically effective amount of peptide selected from calcitonin, insulin, glucagon and somatropin is homogeneously dispersed in and adsorbed onto the carrier selected from hydroxyapatite, calcium carbonate, calcium lactate, magnesium stearate whose mean particle size ranges from 30 µm to 60 µm.

The physiologically effective amount of the physiologically active peptide to be contained in the composition according to the present invention may vary with factors such as the active substance to be chosen, the disease to be treated, desired number of administration, desired effect of therapy, and so on. When administering the composition of the present invention through the nasal cavity, the physiologically effective amount of the physiologically active peptide may be determined on the basis of a comparison of its bioavailability relative to other known preparations cantaining the same active substance.

For example, when insulin is administered subcutaneously to a diabetic patient, the first dose of the insulin usually ranges from 4 insulin unit to 20 insulin unit and the maintenance dose usually ranges from 4 units to 100 units per day, the maximum dose being 800 units per day. Therefore, when administered through nasal route, it is appropriate that the composition be applied at a dose ranging usually from 4 to 100 insulin unit.

Furthermore, when calcitonin, e.g. salmon calcitonin, is administered intramuscularly, a dose ranging from approximately 50 MRC unit (IU) to approximately 100 MRC unit (IU) is applied usually once per day to three times per week. Hence, when administered through nasal route, it is appropriate that the composition be applied at a dose of approximately 50 MRC unit (IU) to approximately 400 MRC unit (IU), preferably from approximately 100 MRC unit (IU) to approximately 200 MRC unit (IU), once per day to three times per week.

The physiologically active peptide composition according to the present invention may contain the physiologically active peptide at a rate of from approximately 0.005% to approximately 30%, preferably from approximately 0.01% to approximately 20%, more preferably from approximately 0.1% to approximately 5.0%, with respect to the total weight of the preparation.

On the other hand, the physiologically active substance composition according to the present invention can achieve high extent of nasal absorption when it contains carrier (for example, hydroxyapatite, calcium carbonate, calcium lactate, magnesium stearate as typical carrier) at a rate of from 70% to approximately 99.995%, preferably from approximately 80% to approximately 99.99%, more preferably from approximately 95% to approximately 99.9%, with respect to the total weight of the preparation.

The physiologically active peptide composition according to the present invention is prepared by homogeneously dispersing a physiologically effective amount of the physiologically active substance having a molecular weight of not more than 40,000 in the unique carrier i.e. physiologically acceptable powdery or crystalline polyvalence metal carrier having a mean particle size of not more than 250 µm, and adsorbing said active substance thereonto.

For example, to prepare the composition according to the present invention, physiologically active peptide as active substance is admixed with carrier, e.g., hydroxyapatite, calcium carbonate or calcium lactate as calcium compound, magnesium stearate as magnesium compound, or aluminum hydroxyide as aluminum compound, in a mortar by applying pressure or shear force to the resulting mixture.

The carrier to be used in the present invention may have a mean particle size of not more than 250 µm, preferably not more than 100 µm and most preferably from approximately 30 µm to approximately 60 µm. On the other hand, it is preferred that the physiologically active peptide is pulverized to the smallest possible particles, the mean particle size being smaller than 20 µm, preferably smaller than 10 µm.

By using the composition according to the present invention, a nasally administrable preparation may be made in such a manner as will be described hereinafter. More specifically, when salmon calcitonin or eel calcitonin is selected as physiologically active peptide, a physiologically effective amount of the calcitonin is admixed with an aqueous solution of pH 4.5 to pH 5.5 containing, as a stabilizing agent, gelatin at a rate of, for example, approximately 1% and aspartic acid at a rate of, for example, approximately 0.1% to 0.5%, preferably approximately 0.38%, and the resulting mixture is then freeze-dried. The resulting powdery mixture is then kneaded at a relative humidity of approximately 55% with hydroxyapatite, thereby yielding fine powder of a nasally administrable composition with the physiologically active peptide adsorbed homogeneously onto the hydroxyapatite.

For another embodiment, when insulin is selected as physiologically active peptide and magnesium stearate is used as the carrier, a physiologically effective amount of the insulin is admixed with an aqueous solution of pH 4.5 to pH 5.5 containing, as a stabilizing agent, gelatin at a rate of, for example, approximately 1% and aspartic acid at a rate of, for example, approximately 0.1% to 0.5%, preferably approximately 0.38%, and the resulting mixture is then freeze-dried. The resulting powdery mixture is then kneaded at a relative humidity of approximately 55% with magnesium stearate, thereby yielding fine powder of a nasally administrable composition with the physiologically active peptide adsorbed homogeneously onto the magnesium stearate.

In order to prevent loss of activity of the physiologically active substance prior to administration, the nasally administrable composition may then be filled in capsules of a low-grease type and packaged in an appropriate form, preferably in a closed form, by combining blister packing with aluminum packaging.

It should be noted that other physiologically active substances may be likewise treated in substantially the same manner as described hereinabove to thereby yield the composition.

As a result of the tests described hereinafter, it was found that a homogeneous humidity of the tested preparation is preferably approximately 55%. This will be described later.

The specific effects offered by the test examples of the nasally administrable physiologically active substance compositions according to the present invention are indicated hereinafter.

TEST EXAMPLE 1

A nasally administrable composition in powdery form was prepared by formulating insulin as a physiologically active peptide at the rate of 2.4 mg/rabbit (5 insulin unit (IU)/rabbit) with hydroxyapatite as a carrier having a mean particle size ranging from 40 to 45 µm.

The resulting composition was nasally administered once to six male New Zealand rabbits.

The average fall of the blood sugar was measured and represented in percentage (%) at 0, 15, 30, 60, 120 and 180 minutes after administration.

For comparison, 2 (IU)/rabbit of insulin was administered subcutaneously to six male New Zealand rabbits and the average fall of the blood sugar was measured and represented in percentage (%) at 0, 60, 120, 240 and 360 minutes after administration.

Table 1 below indicates the average fall of the blood sugar.

TABLE 1

Average fall of the blood sugar

Time for measurement (minutes)

| Nasally form | | | | | | |
|---|---|---|---|---|---|---|
| Present invention | 0 | 15 | 30 | 60 | 120 | 180 |
| | 100% | 105% | 66% | 67% | 84% | 96% |
| S.C. form | | | | | | |
| Comparison | 0 | 60 | 120 | 240 | | 360 |
| | 100% | 57% | 56% | 84% | | 94% |

As is apparent from Table 1 above, it was found that hydroxyapatite was effective to attain a high extent of absorption of insulin through nasal route.

TEST EXAMPLE 2

A nasally administrable composition in powdery form was prepared by formulating salmon calcitonin as a physiologically active peptide at the rate of 200 MRC (IU) per 25 mg with hydroxyapatite as a carrier having a mean particle size ranging from 40 to 45 µm.

The resulting composition was nasally administered once at a dose of 25 mg to three healthy male adults and the blood (2.5 ml) was collected from each of the tested adults prior to administration and then at 5, 10, 15, 20, 30, 45, 60, 90, 120 and 180 minutes after administration. The concentration of the salmon calcitonin in each of the collected blood samples was assayed with a standard RIA assay kit.

Table 2 below indicates the change in concentrations of the salmon calcitonin in the blood.

TABLE 2

Concentration of salmon calcitonin in the blood (pg/ml)

| Sampling time | Concentration of salmon calcitonin in the blood (pg/ml) Case Nos. | | |
|---|---|---|---|
| | No. 1 | No. 2 | No. 3 |
| 0 | ~7 | ~7 | ~7 |
| 5 | 55.50 | 14.05 | 76.25 |
| 10 | 93.05 | 44.12 | 107.67 |
| 15 | 49.84 | 77.03 | 118.26 |
| 20 | 65.95 | 59.36 | 95.07 |
| 30 | 21.08 | 47.69 | 102.78 |
| 45 | 12.54 | 24.68 | 60.68 |
| 60 | 13.50 | 19.43 | 42.97 |
| 90 | 7.92 | ~7 | 21.78 |
| 120 | ~7 | ~7 | 12.75 |
| 180 | ~7 | ~7 | ~7 |

As is apparent from Table 2 above, it was found that the composition in powdery form demonstrated a high degree of absorption of the calcitonin into the blood and, as a result, hydroxyapatite was effective to attain a high extent of absorption of calcitonin.

TEST EXAMPLE 3

A nasally administrable composition in powdery form was prepared by formulating salmon calcitonin as a physiologically active peptide at the rate of 200 MRC (IU) per 25 mg with hydroxyapatite as a carrier having a mean particle size ranging from 40 to 45 µm.

The resulting composition was nasally administered once at a dose of 25 mg to four healthy male adults and the blood (2.5 ml) was collected from each of the tested adults prior to administration and then at 5, 10, 15, 20, 30, 45, 60, 90, 120 and 180 minutes after administration. The concentration of the salmon calcitonin in each of the collected blood samples was assayed with a standard RIA assay kit.

Table 3 below indicates the change in concentrations of the salmon calcitonin in the blood.

TABLE 3

Concentration of salmon calcitonin in the blood (pg/ml)

| Sampling time | Concentration of salmon calcitonin in the blood (pg/ml) Case Nos. | | | |
|---|---|---|---|---|
| | No. 4 | No. 5 | No. 6 | No. 7 |
| 0 | ~7 | ~7 | ~7 | ~7 |
| 5 | 65.30 | 66.02 | 57.83 | 72.72 |
| 10 | 98.88 | 95.22 | 83.75 | 130.21 |
| 15 | 96.96 | 106.69 | 91.55 | 139.54 |
| 20 | 59.91 | 102.60 | 63.17 | 122.29 |
| 30 | 46.96 | 71.13 | 48.09 | 91.38 |
| 45 | 23.89 | 57.42 | 30.95 | 45.91 |
| 60 | 14.31 | 33.21 | 19.56 | 15.62 |
| 90 | ~7 | 13.06 | 10.39 | ~7 |
| 120 | ~7 | 8.76 | ~7 | ~7 |
| 180 | ~7 | ~7 | ~7 | ~7 |

As is apparent from Table 3 above, hydroxyapatite was effective to attain a high extent of absorption of calcitonin through the nasal cavity, the concentration of calcitonin reaching maximum in a short time after administration.

TEST EXAMPLE 4

A nasally administrable composition in powdery form was prepared by formulating salmon calcitonin as a physiologically active peptide at the rate of 200 MRC (IU) per 25 mg with magnesium stearate as a carrier having a mean particle size ranging from 40 to 45 µm.

The resulting composition was nasally administered once at a dose of 25 mg to three healthy male adults and the blood (2.5 ml) was collected from each of the tested adults prior to administration and then at 5, 10, 15, 20, 30, 45, 60, 90, 120 and 180 minutes after administration. The concentration of the salmon calcitonin in each -of the collected blood samples was assayed with a standard RIA assay kit.

Table 4 below indicates the change in concentrations of the salmon calcitonin in the blood.

TABLE 4

| Sampling time | Concentration of salmon calcitonin in the blood (pg/ml) Case Nos. | | |
|---|---|---|---|
| | No. 8 | No. 9 | No. 10 |
| 0 | ~7 | ~7 | ~7 |
| 5 | 60.07 | 25.23 | 29.77 |
| 10 | 50.35 | 16.18 | 33.27 |
| 15 | 37.65 | 24.43 | 41.01 |
| 20 | 34.90 | 15.84 | 30.80 |
| 30 | 22.22 | ~7 | 16.19 |
| 45 | 16.75 | ~7 | 14.79 |
| 60 | 12.60 | ~7 | 14.15 |
| 90 | ~7 | ~7 | 9.42 |
| 120 | ~7 | ~7 | ~7 |
| 180 | ~7 | ~7 | ~7 |

As is apparent from Table 4 above, magnesium stearate was effective to attain a high extent of absorption of calcitonin. The concentration in the blood is thought to be similar to that obtainable by injection.

TEST EXAMPLE 5

A nasally administrable composition in powdery form was prepared by formulating salmon calcitonin as a physiologically active peptide at the rate of 200 MRC (IU) per 25 mg with calcium carbonate as a carrier having a mean particle size ranging from 40 to 45 µm.

The resulting composition was nasally administered once at a dose of 25 mg to three healthy male adults and the blood (2.5 ml) was collected from each of the tested adults prior to administration and then at 5, 10, 15, 20, 30, 45, 60, 90, 120 and 180 minutes after administration. The concentration of the salmon calcitonin in each of the collected blood samples was assayed with a standard RIA assay kit.

Table 5 below indicates the change in concentrations of the salmon calcitonin in the blood.

TABLE 5

| Sampling time | Concentration of salmon calcitonin in the blood (pg/ml) Case Nos. | | |
|---|---|---|---|
| | No. 11 | No. 12 | No. 13 |
| 0 | ~7 | ~7 | ~7 |
| 5 | 59.30 | 40.60 | 73.17 |
| 10 | 71.14 | 121.74 | 70.15 |
| 15 | 83.39 | 131.95 | 66.30 |
| 20 | 76.26 | 113.20 | 65.64 |
| 30 | 44.54 | 46.19 | 46.81 |
| 45 | 25.50 | 38.65 | 27.43 |
| 60 | 13.99 | 13.39 | 16.83 |
| 90 | 13.33 | 16.00 | 14.83 |
| 120 | 7.88 | 12.02 | 13.44 |
| 180 | 7.54 | 8.09 | 8.98 |

As is apparent from Table 5 above, calcium carbonate was effective to attain a high extent of absorption of calcitonin. The concentration in the blood is thought to be similar to that obtainable by injection.

TEST EXAMPLE 6

A nasally administrable composition in powdery form was prepared by formulating salmon calcitonin as a physiologically active peptide at the rate of 200 MRC (IU) per 25 mg with aluminum hydroxide as a carrier having a mean particle size ranging from 40 to 45 µm.

The resulting composition was nasally administered once at a dose of 25 mg to three healthy male adults and the blood (2.5 ml) was collected from each of the tested adults prior to administration and then at 5, 10, 15, 20, 30, 45, 60, 90, 120 and 180 minutes after administration. The concentration of the salmon calcitonin in each of the collected blood samples was assayed with a standard RIA assay kit.

Table 6 below indicates the change in concentrations of the salmon calcitonin in the blood.

TABLE 6

| Sampling time | Concentration of salmon calcitonin in the blood (pg/ml) Case Nos. | | |
|---|---|---|---|
| | No. 14 | No. 15 | No. 16 |
| 0 | ~7 | ~7 | ~7 |
| 5 | 19.75 | 26.41 | 32.23 |
| 10 | 19.35 | 34.82 | 24.85 |
| 15 | 14.97 | 31.66 | 18.68 |
| 20 | ~7 | 37.63 | 12.92 |
| 30 | 9.15 | 24.79 | ~7 |
| 45 | ~8 | 13.70 | ~7 |
| 60 | ~7 | 12.12 | ~7 |
| 90 | ~7 | 8.35 | ~7 |
| 120 | ~7 | ~7 | ~7 |
| 180 | ~7 | 8.26 | ~7 |

As is apparent from Table 6 above, aluminum hydroxide was effective to attain a high extent of absorption of calcitonin. The concentration in the blood is thought to be simlar to that obtainable by injection.

TEST EXAMPLE 7

The carriers to be used in the present invention were tested on the ability to adsorb physiologically active substances.

Hydroxyapatite and magnesium stearate were selected as the carrier, and calcitonin was selected as the physiologically active substance.

Hydroxyapatite (200 mg) having a mean particle size of approximately 40 µm was admixed with salmon calcitonin (5,200 MRC (IU)/mg) having a mean particle size of approximately 15 µm, and pulverized at 4° C. in an agate mortar.

From the powdery mixture, salmon calcitonin unadsorbed on hydroxyapatite was separated and removed and the amount of the salmon calcitonin adsorbed thereon was measured. This was done twice with different samples.

Magnesium stearate (200 mg) having a mean particle size of approximately 40 µm was used instead of hydroxyapatite in the same manner as described above.

For each sample, approximately 10 mg of the powdery mixture was weighed precisely in a glass vessel and to this mixture was added 0.1M acetic acid water solution containing 1% bovine serum albumin (BSA) to make the total amount 100 ml. Then the amount of the salmon calcitonin was measured by salmon calcitonin RIA method.

The results are shown in Table 7 below.

TABLE 7

| Case Nos. (Carrier) | Amount of salmon calcitonin | |
| --- | --- | --- |
|  | ng/mg | MRC/mg |
| No. 1 (hydroxyapatite) | 1,780 | 9.79 |
| No. 2 (hydroxyapatite) | 2,590 | 14.2 |
| No. 3 (magnesium stearate) | 3,290 | 18.1 |
| No. 4 (magnesium stearate) | 2,320 | 12.8 |

Table 7 above shows that hydroxyapatite and magnesium stearate used as the carrier of the present invention demonstrated a high degree of ability to adsorb the physiologically active substance, that is, calcitonin thereon.

TEST EXAMPLE 8

A nasally administrable composition in powdery form was prepared by formulating glucagon (from hog spleen) as a physiologically active peptide at the rate of 40 mg per composition (1,000 mg) with hydroxyapatite as a carrier having a mean particle size ranging from 40 to 45 μm.

The resulting composition was nasally administered once at a dose of 1.2 glucagon unit/30 mg to three healthy male adults and the blood (2.5 ml) was collected from each of the tested adults prior to administration and then at 5, 10, 15, 20, 30, 45, 60, 90, 120, 150 and 180 minutes after administration. The concentration of the glucagon in each of the collected blood samples was assayed with a standard RIA assay kit.

Table 8 below indicates the change in concentrations of the glucagon in the blood.

TABLE 8

Concentration of glucagon in the blood (pg/mg)

| Sampling time | Concentration of glucagon in the blood (pg/ml) Case Nos. | | | |
| --- | --- | --- | --- | --- |
|  | No. 17 | No. 18 | No. 19 | No. 20 |
| 0 | 51 | 46 | 36 | 68 |
| 5 | 73 | 63 | 54 | 97 |
| 10 | 115 | 74 | 79 | 117 |
| 15 | 117 | 85 | 170 | 124 |
| 20 | 97 | 100 | 124 | 121 |
| 30 | 82 | 95 | 86 | 117 |
| 45 | 76 | 98 | 54 | 112 |
| 60 | 63 | 77 | 46 | 106 |
| 90 | 55 | 70 | 29 | 87 |
| 120 | 54 | 73 | 29 | 77 |
| 150 | 58 | 83 | 26 | 71 |
| 180 | 42 | 68 | 27 | 78 |

As is apparent from Table 8 above, it was found that hydroxyapatite was effective to attain a high extent of absorption of glucagon through nasal route.

TEST EXAMPLE 9

A nasally administrable composition in powdery form was prepared by formulating glucagon (from hog spleen) as a physiologically active peptide at the rate of 40 mg per composition (1,000 mg) with calcium carbonate as a carrier having a mean particle size ranging from 40 to 45 μm.

The resulting composition was nasally administered once at a dose of 1.2 glucagon unit/30 mg to three healthy male adults and the blood (2.5 ml) was collected from each of the tested adults prior to administration and then at 5, 10, 15, 20, 30, 45, 60, 90, 120, 150 and 180 minutes after administration. The concentration of the glucagon in each of the collected blood samples was assayed with a standard RIA assay kit.

Table 9 below indicates the change in concentrations of the glucagon in the blood.

TABLE 9

Concentration of glucagon in the blood (pg/mg)

| Sampling time | Concentration of glucagon in the blood (pg/ml) Case Nos. | | | |
| --- | --- | --- | --- | --- |
|  | No. 21 | No. 22 | No. 23 | No. 24 |
| 0 | 34 | 56 | 42 | 48 |
| 5 | 73 | 79 | 80 | 53 |
| 10 | 97 | 91 | 80 | 44 |
| 15 | 86 | 79 | 83 | 53 |
| 20 | 85 | 89 | 82 | 50 |
| 30 | 71 | 77 | 90 | 55 |
| 45 | 73 | 89 | 76 | 49 |
| 60 | 64 | 79 | 77 | 46 |
| 90 | 62 | 78 | 73 | 47 |
| 120 | 56 | 79 | 88 | 46 |
| 150 | 52 | 67 | 79 | 54 |
| 180 | 51 | 66 | 62 | 50 |

As is apparent from Table 9 above, it was found that calcium carbonate was effective to attain a high extent of absorption of glucagon through nasal route.

TEST EXAMPLE 10

A nasally administrable composition in powdery form was prepared by formulating somatropin (growth hormone; recombinant type—NOVO) as a physiologically active peptide at the rate of 150 mg per composition (1,000 mg) with hydroxyapatite (or calcium carbonate) as a carrier having a mean particle size ranging from 40 to 45 μm.

The resulting composition was nasally administered once at a dose of 6.825 somatropin unit/25 mg of hydroxyapatite to two healthy male adults and 6.825 somatropin unit/25 mg of calcium carbonate to other two healthy male adults.

The blood (2.5 ml) was collected from each of the tested adults prior to administration and then at 5, 10, 15, 20, 30, 45, 60, 90, 120 and 150 minutes after administration. The concentration of the somatropin in each of the collected blood samples was assayed with an immunoradiometric assay (IRMA) kit.

Table 10 below indicates the change in concentrations of the somatropin in the blood.

TABLE 10

Concentration of somatropin in the blood (ng/mg)

| Sampling time | Concentration of somatropin in the blood (ng/ml) Case Nos. | | | |
|---|---|---|---|---|
| | hydroxyapatite | | calcium carbonate | |
| | No. 25 | No. 26 | No. 27 | No. 28 |
| 0 | 0.49 | 0.76 | 0.28 | 0.24 |
| 5 | 2.44 | 3.18 | 0.96 | 0.55 |
| 10 | 3.59 | 2.27 | 2.55 | 1.08 |
| 15 | 4.66 | 2.00 | 2.84 | 1.41 |
| 20 | 6.25 | 1.86 | 3.02 | 1.78 |
| 30 | 5.21 | 1.67 | 4.11 | 1.91 |
| 45 | 4.16 | 1.80 | 8.93 | 1.99 |
| 60 | 2.93 | 1.61 | 13.10 | 2.11 |
| 90 | 1.45 | 1.41 | 14.60 | 1.27 |
| 120 | 0.76 | 1.16 | 5.65 | 0.92 |
| 150 | 0.54 | 0.91 | 2.97 | 0.80 |

As is apparent from Table 10 above, it was found that hydroxyapatite and calcium carbonate were effective to attain a high extent of absorption of somatropin (growth hormone) through nasal route.

TEST EXAMPLE 11

A nasally administrable composition in powdery form was prepared by formulating somatropin (growth hormone; recombinant type—NOVO) as a physiologically active peptide at the rate of 150 mg per composition (1,000 mg) with calcium lactate (or calcium carbonate) as a carrier having a mean particle size ranging from 40 to 45 µm.

The resulting composition was nasally administered once at a dose of 6,825 somatorpin unit/25 mg of calcium lactate to two healthy male adults and 6.825 somatropin unit/25 mg of calcium carbonate to other two healthy male adults.

The blood (2.5 ml) was collected from each of the tested adults prior to administration and then at 5, 10, 15, 20, 30, 45, 60, 90, 120, 150 and 180 minutes after administration. The concentration of the somatropin in each of the collected blood samples was assayed with an immunoradiometric assay (IRMA) kit.

Table 11 below indicates the change in concentrations of the somatropin in the blood.

TABLE 11

Concentration of somatropin in the blood (ng/mg)

| Sampling time | Concentration of somatropin in the blood (ng/ml) Case Nos. | | | |
|---|---|---|---|---|
| | calcium lactate | | calcium carbonate | |
| | No. 29 | No. 30 | No. 31 | No. 32 |
| 0 | 1.15 | 0.16 | 0.15 | 0.69 |
| 5 | 2.56 | 0.30 | 0.46 | 6.15 |
| 10 | 4.29 | 0.37 | 0.81 | 2.81 |
| 15 | 5.11 | 0.65 | 1.13 | 2.49 |
| 20 | 5.87 | 0.72 | 1.30 | 2.20 |
| 30 | 7.70 | 0.79 | 1.64 | 2.12 |
| 45 | 5.99 | 0.71 | 1.79 | 1.67 |
| 60 | 6.16 | 0.62 | 1.47 | 1.36 |
| 90 | 3.39 | 0.58 | 1.18 | 1.02 |
| 120 | 1.70 | 0.32 | 0.79 | 0.48 |
| 150 | 0.84 | 0.24 | 0.59 | 0.37 |
| 180 | 0.45 | 1.02 | 1.67 | 0.48 |

As is apparent from Table 11 above, it was found that calcium lactate and calcium carbonate were effective to attain a high extent of absorption of somatropin (growth hormone) through nasal route.

TEST EXAMPLE 12

A nasally administrable composition in powdery form was prepared by formulating glucagon (from hog spleen) as a physiologically active peptide at the rate of 40 mg per composition (1,000 mg) with calcium carbonate as a carrier having a mean particle size ranging from 40 to 45 µm.

The resulting composition was nasally administered once at a dose of 0.4 glucagon unit/30 mg to two healthy male adults and 2 glucagon unit/30 mg to another two healthy male adults, and the blood (2.5 ml) was collected from each of the tested adults prior to administration and then at 5, 10, 15, 20, 30, 45, 60, 90, 120, 150 and 180 minutes after administration. The concentration of the glucagon in each of the collected blood samples was assayed with a standard RIA assay kit.

Table 12 below indicates the change in concentrations of the glucagon in the blood.

TABLE 12

Concentration of glucagon in the blood (pg/mg)

| Sampling time | Concentration of glucagon in the blood (pg/ml) Case Nos. | | | |
|---|---|---|---|---|
| | 0.4 glucagon unit | | 2 glucagon unit | |
| | No. 33 | No. 34 | No. 35 | No. 36 |
| 0 | 112 | 60 | 53 | 97 |
| 5 | 115 | 65 | 76 | 109 |
| 10 | 119 | 77 | 116 | 104 |
| 15 | 130 | 72 | 85 | 96 |
| 20 | 127 | 79 | 102 | 118 |
| 30 | 116 | 86 | 56 | 100 |
| 45 | 121 | 75 | 94 | 105 |
| 60 | 137 | 61 | 79 | 122 |
| 90 | 122 | 66 | 60 | 117 |
| 120 | 108 | 57 | 69 | 99 |
| 150 | 111 | 76 | 69 | 106 |
| 180 | 110 | 74 | 60 | 105 |

As is apparent from Table 12 above, it was found that calcium carbonate was effective to attain a high extent of absorption of glucagon through nasal route.

As described hereinabove, the physiologically active substance compositions according to the present invention allows physiologically active peptides, which are unlikely or difficult to be orally administered, to be administered through a nasal route with high absorbability and without irritation.

In particular, when the composition in powdery form having the physiologically active peptide such as calcitonin, insulin, glucagon or somatropin dispersed in the specific carrier of the present invention—for example, hydroxyapatite, calcium carbonate, calcium lactate, magnesium stearate or aluminum hydroxide—is administered through the nasal route, that is, when it is applied to the mucous membrane of the nasal cavity, the physiologically active peptide is well absorbed into the body to show high clinical effects.

What is claimed is:

1. A nasally administrable composition comprising a physiologically active substance having a molecular weight of not more than 40,000 and a physiologically acceptable powdery or crystalline polyvalence metal carrier, wherein a physiologically effective amount of said physiologically active substance is dispersed homogeneously in and adsorbed homogeneously onto said polyvalence metal carrier, and a mean particle size of said polyvalence metal carrier is not more than 250 µm.

2. A nasally administrable composition as claimed in claim 1, wherein said polyvalence metal carrier is divalence metal compound selected from the group consisting of aluminum compound, calcium compound, magnesium compound, silicon compound, iron compound and zinc compound.

3. A nasally administrable composition as claimed in claim 2, wherein said aluminum compound is selected from the group consisting of dry aluminum hydroxy gel, aluminum hydroxychloride, synthetic aluminum silicate, light aluminum oxide, colloidal aluminum silicate hydrate, aluminum magnesium hydroxide, aluminum hydroxide, aluminum hydroxide gel, aluminum sulfate, dihydroxyaluminum aminoacetate, aluminum stearate, natural aluminum silicate, aluminum monostearate and potassium aluminum sulfate.

4. A nasally administrable composition as claimed in claim 2, wherein said calcium compound is selected from the group consisting of apatite, hydroxyapatite, calcium carbonate, calcium disodium EDTA, calcium chloride, calcium citrate, calcium glycerophosphate, calcium gluconate, calcium silicate, calcium oxide, calcium hydroxide, calcium stearate, calcium phosphate tribasic, calcium lactate, calcium pantothenate, calcium oleate, calcium palmirate, calcium D-pantothenate, calcium alginate, calcium phosphate anhydride, calcium hydrogenphosphate, calcium primary phosphate, calcium acetate, calcium saccharate, calcium sulfate, calcium secondary phosphate, calcium para-aminosalicylate, and bio calcilutite compounds.

5. A nasally administrable composition as claimed in claim 2, wherein said magnesium compound is selected from the group consisting of magnesium L-aspartate, magnesium chloride, magnesium gluconate, magnesium aluminate silicate, magnesium silicate, magnesium oxide, magnesium hydroxide, magnesium stearate, magnesium carbonate, magnesium aluminate metasilicate, magnesium sulfate, sodium magnesium silicate and synthetic sodium magnesium silicate.

6. A nasally administrable composition as claimed in claim 2, wherein said silicon compound is selected from silicon Oxide hydrate, light silicic anhydride, synthetic hydrotalcite, diatomaceous earth and silicon dioxide.

7. A nasally administrable composition as claimed in claim 2, wherein said iron compound is ferrous sulfate.

8. A nasally administrable composition as claimed in claim 2, wherein said zinc compound is selected from zinc chloride, zinc stearate, zinc oxide and zinc sulfate.

9. A nasally administrable composition as claimed in claim 4, wherein said calcium compound is hydroxyapatite, calcium carbonate or calcium lactate.

10. A nasally administrable composition as claimed in claim 5, wherein said magnesium compound is magnesium stearate.

11. A nasally administrable composition as claimed in claim 3, wherein said aluminum compound is aluminum hydroxide.

12. A nasally administrable composition as claimed in claim 1, wherein said polyvalence metal carrier has a mean partice size of not more than 100 µm.

13. A nasally administrable composition as claimed in claim 12, wherein a mean particle size of said polyvalence metal carrier ranges from 30 µm to 60 µm.

14. A nasally administrable composition as claimed in claim 1, wherein the physiologically active substance having a molecular weight of not more than 40,000 is any one of compound selected from the group consisting of physiologically active peptide, hypnotics and sedatives, anti-epileptics, minor tranquilizers, major tranquilizers, antidepressants, muscle relaxants, anti-allergic agents, antirheumatics, cardiotonics, antiarrhythmics, antihypertensive diuretics, α-blocking agents, β-adrenergic agents, calcium channel antagonists, angiotensin converting enzyme inhibitors, antihypertensives, coronary vasodilators, cerebral circulation and metabolism ameliorators, anti-arteriosclerotics, cardiovascular agents, bronchodilators, anti-ulceratives, antiemetics, antiobesity agents, platelet aggregation inhibitors, antidiabetics/symptomatic antidiabetics, adrenocortical hormones and DNA/RNA compounds.

15. A nasally administrable composition as claimed in claim 14, wherein a physiologically active substance is a physiologically active peptide.

16. A nasally administrable composition comprising a physiologically active peptide and a physiologically acceptable powdery or crystalline polyvalence metal carrier, wherein a physiologically effective amount of said physiologically active peptide is dispersed homogeneously in and adsorbed homogeneously onto said polyvalence metal carrier, and a mean particle size of said polyvalence metal carrier is not more than 250 µm.

17. A nasally administrable composition as claimed in claim 16, wherein said polyvalence metal carrier is any one of divalence metal compounds selected from the compound selected from the group consisting of aluminum compound, calcium compound, megnesium compound, silicon compound, iron compound and zinc compound.

18. A nasally administrable composition as claimed in claim 17, wherein said divalence metal carrier is any one of the carriers selected from the group consisting of dry aluminum hydroxy gel, aluminum hydroxychloride, synthetic aluminum silicate, light aluminum oxide, colloidal aluminum silicate hydrate, aluminum magnesium hydroxide, aluminum hydroxide, aluminum hydroxide gel, aluminum sulfate, dihydroxyaluminum aminoacetate, aluminum stearate, natural aluminum silicate, aluminum monostearate and potassium aluminum sulfate.

19. A nasally administrable composition as claimed in claim 17, wherein a mean particle size of said carrier is not more than 100 µm.

20. A nasally administrable composition as claimed in claim 19, wherein a mean paraticle size of said carrier ranges from 30 µm to 60 µm.

21. A nasally administrable composition as claimed in claim 16, wherein said physiologically active peptide is a peptide hormone, a physiologically active protein or an enzymatic protein.

22. A nasally administrable composition as claimed in claim 21, wherein said peptide hormone is selected from calcitonin, insulin, glucagon and growth hormone (somatropin).

23. A nasally administrable composition as claimed in claim 22, wherein said calcitonin is dispered homogeneously in and adsorbed homogeneously onto any one of carrier selected from the group consisting of hydroxyapatite, calcium carbonate, calcium lactate, magnesium stearate and aluminun hydroxide, wherein said carrier has a mean particle size ranging from 30 μm to 60 μm.

24. A nasally administrable composition as claimed in claim 22, wherein said insulin is dispered homogeneously in and adsorbed homogeneously onto any one of carrier selected from the group consisting of hydroxyapatite, calcium carbonate, calcium lactate, magnesium stearate and aluminun hydroxide, wherein said carrier has a mean particle size ranging from 30 μm to 60 μm.

25. A nasally administrable composition as claimed in claim 22, wherein said glucagon is dispered homogeneously in and adsorbed homogeneously onto any one of carrier selected from the group consisting of hydroxyapatite, calcium carbonate, calcium lactate, magnesium stearate and aluminun hydroxide, wherein said carrier has a mean particle size ranging from 30 μm to 60 μm.

26. A nasally administrable composition as claimed in claim 22, wherein said somatropin is dispered homogeneously in and adsorbed homogeneously onto any one of carrier selected from the group consisting of hydroxyapatite, calcium carbonate, calcium lactate, magnesium stearate and aluminun hydroxide, wherein said carrier has a mean particle size ranging from 30 μm 60 μm.

* * * * *